United States Patent
Cooper et al.

(10) Patent No.: US 6,897,781 B2
(45) Date of Patent: May 24, 2005

(54) ELECTRONIC PATIENT MONITOR AND WHITE NOISE SOURCE

(75) Inventors: Craig L. Cooper, Inola, OK (US); Toby E. Smith, Broken Arrow, OK (US)

(73) Assignee: Bed-Check Corporation, Tulsa, OK (US)

( * ) Notice: Subject to any disclaimer, the term of this patent is extended or adjusted under 35 U.S.C. 154(b) by 208 days.

(21) Appl. No.: 10/397,126

(22) Filed: Mar. 26, 2003

(65) Prior Publication Data

US 2004/0189475 A1 Sep. 30, 2004

(51) Int. Cl.[7] .............................................. G08B 23/00
(52) U.S. Cl. .............................. 340/573.1; 340/573.7; 340/686.1; 340/686.6; 340/517; 381/71.1; 600/28
(58) Field of Search ........................ 340/573.1, 573.7, 340/686.1, 686.6, 517; 381/71.1; 600/28; 128/845

(56) References Cited

U.S. PATENT DOCUMENTS

| | | | |
|---|---|---|---|
| 3,712,292 A | * 1/1973 | Zentmeyer, Jr. ............. 600/28 |
| 4,020,482 A | 4/1977 | Feldl | |
| 4,633,237 A | 12/1986 | Tucknott et al. | |
| 5,319,355 A | 6/1994 | Russek | |
| 5,448,996 A | 9/1995 | Bellin et al. | |
| 5,534,851 A | 7/1996 | Russek | |
| 5,619,179 A | 4/1997 | Smith | |
| 5,676,633 A | 10/1997 | August | |
| 5,838,244 A | * 11/1998 | Schmidt et al. ............. 340/635 |
| 5,844,996 A | * 12/1998 | Enzmann et al. .......... 381/71.6 |
| 6,035,047 A | * 3/2000 | Lewis .......................... 381/72 |
| 6,111,509 A | 8/2000 | Holmes | |
| 6,307,476 B1 | 10/2001 | Smith et al. | |
| 6,320,510 B2 | 11/2001 | Menkedick et al. | |
| 6,359,549 B1 | 3/2002 | Lau et al. | |
| 6,384,728 B1 | * 5/2002 | Kanor et al. ............. 340/573.1 |
| 6,721,706 B1 | * 4/2004 | Strubbe et al. ............. 704/275 |
| 6,728,679 B1 | * 4/2004 | Strubbe et al. .......... 704/270.1 |
| 6,731,307 B1 | * 5/2004 | Strubbe et al. ............. 715/727 |
| 6,795,808 B1 | * 9/2004 | Strubbe et al. ............. 704/275 |
| 2003/0010345 A1 | * 1/2003 | Koblasz et al. ............. 128/845 |
| 2003/0181949 A1 | * 9/2003 | Whale .......................... 607/2 |
| 2004/0004559 A1 | * 1/2004 | Rast ............................. 341/34 |
| 2004/0234080 A1 | * 11/2004 | Hernandez et al. ...... 381/71.11 |

* cited by examiner

Primary Examiner—Benjamin C. Lee
(74) Attorney, Agent, or Firm—Fellers, Snider, Blankenship, Bailey & Tippens, P.C.; Terry L. Watt (57) ABSTRACT

According to a preferred embodiment, there is provided an electronic patient monitor for use in reducing the risk of decubitus ulcers. The monitor utilizes a separate sensor which senses the position of the patient in the bed or chair for purposes of determining when the patient moves. Additionally, the monitor broadcasts masking noise through its own, or through a remote, speaker, thereby enabling the patient to rest more comfortably in a noisy institutional environment. If the patient does not move on his or her own accord within a predetermined turn interval, the masking sound broadcast will be terminated which will gently encourage the patient to move. An alarm may additionally be sounded to notify the caregiver that the patient needs to be manually turned to reduce the risk of decubitus ulcers.

17 Claims, 6 Drawing Sheets

ELECTRONIC PATIENT MONITOR AND WHITE NOISE SOURCE

This invention relates generally to monitoring systems and more particularly concerns devices and systems used to monitor seated or lying patients in homes or in medical environments such as hospitals, institutions, and other caregiving environments.

BACKGROUND OF THE INVENTION

It is well known that patients who are confined to a bed or chair for extended periods of time are at risk of developing decubitus ulcers, i.e., pressure sores, or bed sores as they are more commonly known. These ulcers are often seen to develop within soft tissue that is compressed between a bed or chair surface and a patient's weight-bearing bony prominences, the compressed tissue being at least partially of deprived of oxygenated blood flow. A continued lack of blood flow, and resultant lack of oxygen, can result in cell death which may be evidenced in the form of pressure sores. Pressure sores do not develop immediately, but rather form over time, with the development speed depending on a number of factors including the firmness and friction of the supporting surface against the patient's skin, the patient/ambient temperature, blood pressure, the amount of moisture in contact with the skin, and the health and susceptibility of the skin due to age or illness.

One venerable and generally accepted means of reducing the risk of decubitus ulcer development in bedfast patients is to turn them regularly, usually at approximately two hour intervals. For example, a patient in a back rest position might be periodically rolled to one side or the other, such motion helping to maintain blood to flow to soft tissue that is under compression. Similar strategies are employed for patients that are confined to a chair for long periods of time. Obviously, an assisted-movement strategy relies to a large extent on the vigilance of the (often harried) attending staff to insure that the patient is properly relocated.

However, to the extent that the patient has some capacity for self movement, the patient should be encouraged to turn himself or herself. However, even if the patient has recently moved under his/her own power, the staff will generally not recognize that fact and will turn the patient again at the next scheduled time. This means that the patient may be roused from a sound slumber to be turned even if that is not really necessary. Since the typical turn interval is about every two hours, it should be clear that it can be difficult under normal circumstances for a patient that might be at risk of bed sores to get much rest.

Of course, as important as rest might be to a convalescing patient, it can be proved to be difficult to rest in an institutional environment such as a hospital, nursing home, etc. That is, in a hospital or nursing home there is near-constant activity and such activity continues during both day and night. Of course, the ill and recovering patients desperately needs uninterrupted sleep which may be elusive in such a setting.

In this context, it is well known that a relatively constant-level sound source such as "white noise" can mask low-level background noises and has the potential to help an individual sleep uninterruptedly. White noise and similar sounds have been used to assist patients with insomnia, restlessness, sleeplessness, tinnitus, ADD/ADHD, and hyperacusis get to sleep. Sources of such "noise" are found in nature (e.g., the sound of ocean waves, a babbling brook, rain, etc.), in technology (fans, air conditioners, etc.), and they can be mathematically generated according to algorithms well known to those of ordinary skill in the art. However, in any case, the consequences of introducing such a sound source into the patient's environment can result in a dramatic improvement in sleep quality. Obviously, to the extent that the patient rests more soundly he or she will be less likely to rise from the bed or other support surface, thus reducing the likelihood of an injurious fall.

Whether it be for purposes of fall prevention, detection of wetness, or any other reason a chronic shortage of caregivers has resulted in an increasing reliance on microprocessor-based monitoring of patients. Indeed, in the area of decubitus ulcers some advances have been made in recent years, but those inventions typically have to do with notifying caregivers that a patient needs to be moved and/or automatically adjusting the bed to shift the patient's weight distribution.

Thus, what is needed is an electronic patient monitor that encourages a bedfast patient to move on his or her own and, if that does not happen, notifies the caregiver that the patient needs to be turned. Additionally, and more generally, what is needed is an electronic patient monitor that can create masking sounds to help the patient sleep more soundly.

Heretofore, as is well known in the patient monitor arts, there has been a need for an invention to address and solve the above-described problems and, more particularly, there has been a need for an electronic device that functions both as a patient monitor and as a white-noise source for purposes assisting the monitored patient monitored rest more completely in an institutional environment or elsewhere. Accordingly, it should now be recognized, as was recognized by the present inventors, that there exists, and has existed for some time, a very real need for a system for monitoring patients that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided an electronic patient monitor that additionally is equipped with at least one speaker for broadcasting white noise or similarly steady sound series for purposes of masking ambient sounds/noise.

According to a first preferred embodiment, there is provided an electronic patient monitor that senses the position of a patient through an attached sensing device and encourages that patient to move in the bed or chair at regular intervals according to the following preferred method. The patient monitor will be equipped with a white noise generator or similar sound source that, upon activation, will tend to cover intrusive ambient sounds generated by others. The presence of the masking sound will make it easier for the patient to fall asleep. Preferably the attached monitor will additionally contain a time/clock chip or similar means of determining elapsed time. Given a predetermined turn interval, the instant invention then continues to monitor the patient's position and maintains its generation of masking sounds until the expiration of the turn interval, at which time it will turn off the white noise generator and begin to sound a soft alarm or similar prompting sound (e.g., a voice that directs the patient to turn) that is intended to rouse the patient to turn and/or to notify a caregiver that the patient should be manually turned. Preferably, the soft alarm will be followed after some period of time with a louder alarm if the patient does not move, say, within five minutes.

In the event that the patient moves before the expiration of the predetermined time interval and, thus, would not need to be manually turned at the designated time, the monitor will sense that fact and reset its timer. The white noise generator will then continue to play until the turn time interval has lapsed again. If the patient does not move during this second (or any subsequent) time period, the monitor will again sound its alarm, thus ensuring that the patient is turned on schedule if he/she has not been able to turn himself or herself in the meantime.

According to another preferred embodiment, there is provided a patient monitor contains a white noise (masking noise) generator therein and wherein the attached sensor is one that is designed to detect patient presence or absence (e.g., a conventional pressure sensitive mat). In a preferred arrangement, the white noise generator will be manually activated in order to help the patient sleep more comfortably. Then, if the patient seeks to leave the bed, the white noise generator will be silenced and the exit alarm will sound.

According to still another preferred embodiment, there is provided an electronic patient monitor that contains a white noise generator wherein the frequency, amplitude, etc. of the white noise is adaptively determined by reference to the sonic characteristics of the ambient noise in the patient's room. That is, in a preferred arrangement the patient monitor is designed to determine at least approximately the sonic characteristics of incident ambient noise by taking a digital recording of the sound reaching the monitor and, presumably also, the patient. Given that information, it is possible to calculate estimates of the amplitude, frequency content, phase, etc., of the ambient sound and then to shape the sonic characteristics of the white noise to at least approximately match those of the ambient noise, thereby obscuring that noise as much as is possible.

According to another preferred embodiment of the instant invention, there is provided hereinafter an apparatus for patient monitoring that includes a sensor positionable to be proximate to the patient and designed to be responsive to a patient condition. In electronic communication with the sensor is a microprocessor-controlled patient monitor that responds to the patient sensor according to its internal programming. The patient monitor contains a speaker for the broadcast of alarm sounds and for the further broadcast of masking sounds that are issued under control of the microprocessor. In the preferred embodiment, the masking sounds will have been synthesized by the microprocessor, but that is not strictly necessary and other arrangements are certainly possible. Additionally, it is preferable that a single speaker be used for both alarm and masking sounds, but it should be clear that multiple speakers could be used with, for example, one for alarm sounds and another for masking sounds. Finally, it is economically preferable that a single microprocessor monitor the status of the with the patient sensor and initiate/control the production of masking sounds. However, it should be clear that the work could be divided among multiple CPUs if that were desired.

According to another preferred arrangement, there is provided a patient monitor substantially as described above, but wherein the volume of the alarm is varied depending on whether it is day or night. That is, during the evening sounds within the facility might be expected to generally be lower and the masking/white noise need not be so loud to cover them. Thus, according to the instant embodiment the volume is changed depending on the time of day and/or the amount of ambient light, wherein preferably the volume of the white noise is increased during the day and decreased during the evening/night hours.

According to still another preferred arrangement, there is provided an electronic patient monitor substantially as described above, wherein the masking sounds are automatically terminated when the patient exit alarm is activated.

According to a further preferred embodiment, there is provided an electronic patient monitor substantially as described above, but wherein the white noise is tunable to a particular center frequency to mask specific sorts of ambient noise.

According to still a further preferred embodiment, there is provided a electronic patient monitor substantially as described above, but wherein the monitor has at least two different operating "modes": a first mode wherein the patient's unassisted/independent movement is evaluated ("evaluation" mode), and a second mode wherein the patient is continuously monitored and the white noise generator is activated or not depending on the patient's current activities as measured against the level of activity observed during the evaluation phase.

According to a further embodiment, there is provided a electronic patient monitor substantially as described above, but wherein the "white noise" takes the form of a recording (either digital or analog) of the ambient sounds at the patient's home. In one preferred arrangement, the patient (or his/her family if the patient is already hospitalized) will make a digital recording of ambient house sounds (e.g., refrigerator, dish washer, washing machine, dryer, animals in or around the house, air conditioner/heater, etc) for use by the instant invention. The recording will then be transferred to the instant electronic monitor where it is preferably held in digital form within the memory of the monitor until such time as it would be appropriate to play "white noise" for the patient. During such playback, one of two possible modes will preferably be employed. In a first mode, the patient's own home sounds will be played at a level that masks facility noise, thereby replacing unfamiliar ambient sounds with more familiar ones. In a second preferred mode, conventional white noise will be played together with the patient's own ambient home sounds, thereby more completely masking intrusive noises at the facility. That is, in this mode the electronic monitor will digitally combine the recording from the patient's home with a "true" randomly generated white noise "background" to create a sound source. The true white noise tends to blocks the facility sounds and the other sounds make the patient more comfortable by providing sounds that are familiar to him or her, albeit in another setting.

In still another preferred arrangement, there is provided an electronic patient monitor that uses active noise cancellation in concert with—or as an alterative to—white noise generation. That is, there is provided hereinafter a patient monitor substantially as described above but wherein the monitor contains an active noise reduction system to reduce the level ambient noise experienced by the patient. Although this might be implemented in many ways, a preferred arrangement a separate microphone located between the patient and the door will pick up ambient noise from the facility on its way to the patient. The monitor will then generate and broadcast sound that is 180 degrees out of phase with that coming in through the door, thereby reducing the level of ambient noise experienced by the patient. Of course, such technology could be used, not only to reduce the level of noise received from outside the room, but to reduce the noise level within the room where, for example, one patient in a multi-occupancy room is disturbed by the snoring of a roommate.

Finally, and according to still another preferred embodiment, there is provided an electronic patient monitor substantially as described above, but wherein the electronic patient monitor contains a microphone and wherein the center frequency of the white noise is adaptively tunable under software control to match ambient noise in the environment, thereby masking most heavily those noise frequencies that are actually perceptible in the patient's room.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to apply to all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

According to a preferred aspect of the instant invention, there is provided an electronic patient monitor for use with a patient sensor, wherein the monitor contains at least one speaker for generating white noise or similar masking sounds and which is designed to assist the patient in sleeping. Additionally, the instant invention is preferably designed to operate as—or in a conjunction with—a patient exit system to monitor the presence or absence of a patient in a bed or chair.

General Environment of the Invention

Figure 1:
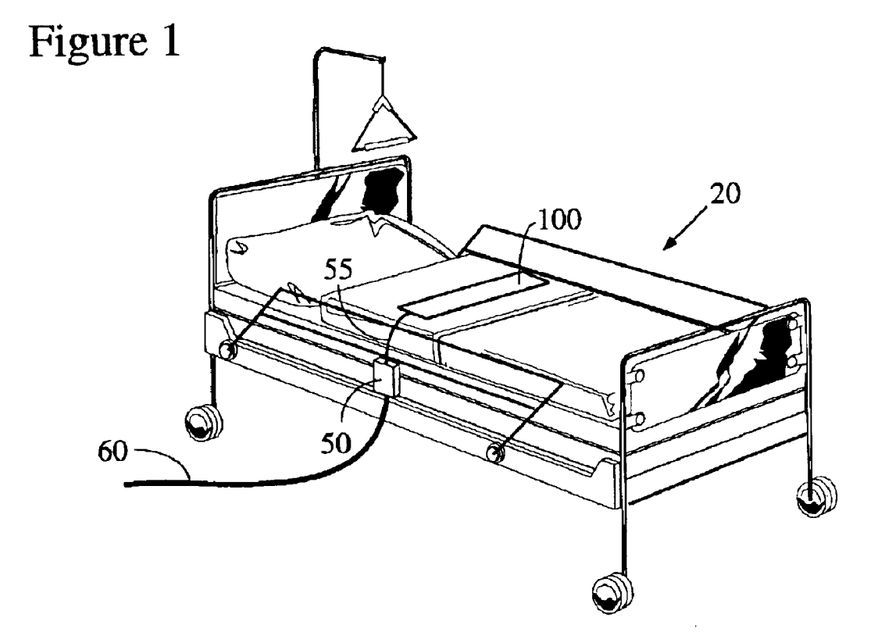
FIG. 1 illustrates the general environment of the instant invention, wherein an electronic patient monitor is connected to a bed mat.

Generally speaking, electronic patient monitors of the sort discussed herein work by first sensing an initial status of a patient, and then generating a signal when that status changes (e.g., the patient changes position from laying or sitting to standing, the sensor changes from dry to wet, etc.). Turning now to FIG. 1 wherein the general environment of one specific embodiment of the instant invention is illustrated, in a typical arrangement a pressure sensitive mat 100 sensor is placed on a hospital bed 20 where it will lie beneath a weight-bearing portion of the reclining patient's body, usually the buttocks and/or shoulders. Generally speaking, the mat 100/electronic monitor 50 combination works as follows. When a patient is placed atop the mat 100, the patient's weight compresses it, thereby closing an internal electrical circuit. This circuit closure is sensed by the attached electronic patient monitor 50 and, depending on its design, this closure may signal the monitor 50 to begin monitoring the patient via the mat 100. Additionally, in some embodiments, the monitoring phase is initiated by a manually engaged switch. Thereafter, when the patient attempts to leave the bed, weight is removed from the sensing mat 100, thereby breaking the electrical circuit, which interruption is sensed by the attached electronic patient monitor 50. The patient monitor 50, which conventionally contains a microprocessor therein, then signals the caregiver per its pre-programmed instructions. In some cases, the signal will amount to an audible alarm or siren that is emitted from the unit 50. In other cases, an electronic signal could be sent to a remote nurses/caregivers station via electronic communications line 60. Note that additional electronic connections not pictured in this figure might include a monitor power cord to provide a source of AC power although, as generally pictured in this figure, the monitor 50 can certainly be configured to be either battery or AC powered.

Figure 2:
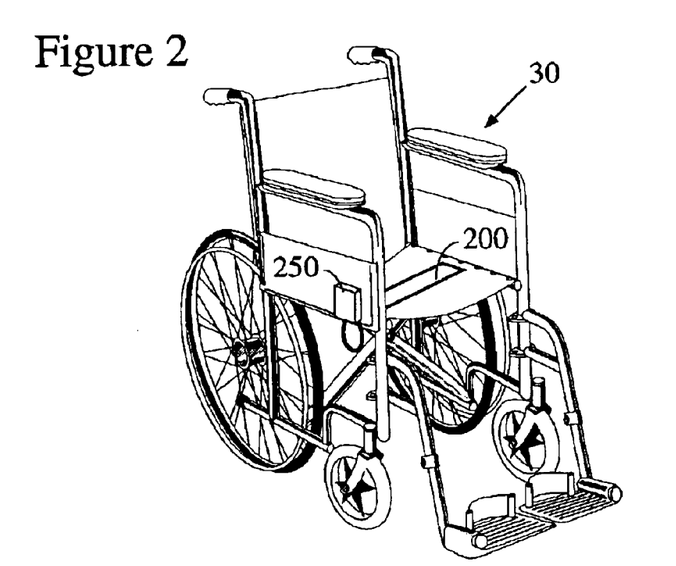
FIG. 2 illustrates the general environment of the instant invention, wherein an electronic patient monitor is connected to a chair mat.

In another common arrangement, and as is illustrated in FIG. 2, a pressure sensitive chair sensor 200 might be placed in the seat of a wheel chair or the like for purposes of monitoring a patient seated therein. As has been described previously, a typical configuration utilizes a pressure sensitive mat 200 which is connected to electronic chair monitor 250 that is attached to the chair 30. Because it is anticipated that the patient so monitored might choose to be at least somewhat mobile, the monitor 250 will usually be battery powered and will signal a chair-exit event via an internal speaker, rather than a nurse-call interface.

General information relating to mat sensors and electronic monitors for use in patient monitoring may be found in U.S. Pat. Nos. 4,179,692, 4,295,133, 4,700,180, 5,600,108, 5,633,627, 5,640,145, 5,654,694, and 6,111,509 (the last of which concerns electronic monitors generally). Additional information may be found in U.S. Pat. Nos. 4,484,043, 4,565,910, 5,554,835, 5,623,760, 6,417,777 (sensor patents) and U.S. Pat. No. 5,065,727 (holsters for electronic monitors), the disclosures of all of which patents are all incorporated herein by reference. Further, U.S. Pat. No. 6,307,476 (discussing a sensing device which contains a validation circuit incorporated therein), and U.S. patent Ser. No. 09/944,622, (for automatically configured electronic monitor alarm parameters), and Ser. No. 10/125,059 (for a lighted splash guard) are similarly incorporated herein by reference.

Note that the instant invention is suitable for use with a wide variety of patient sensors in addition to pressure sensing switches including, without limitation, temperature sensors, patient activity sensors, toilet seat sensors (see, e.g., U.S. Pat. No. 5,945,914), wetness sensors (e.g., U.S. Pat. No. 6,292,102), decubitus ulcer sensors (e.g., U.S. patent application Ser. No. 09/591,887), etc. Thus, in the text that follows the terms "mat" or "patient sensor" should be interpreted in its broadest sense to apply to any sort of patient monitoring switch or device, whether the sensor is pressure sensitive or not.

Preferred Embodiments

According to a first preferred embodiment, there is provided an electronic patient monitor that senses the position of a patient who is resting in a bed, chair, or other support surface and which utilizes broadcast sound to encourage that patient to move at regular intervals so as to help prevent the occurrence of decubitus ulcers.

Figure 3:
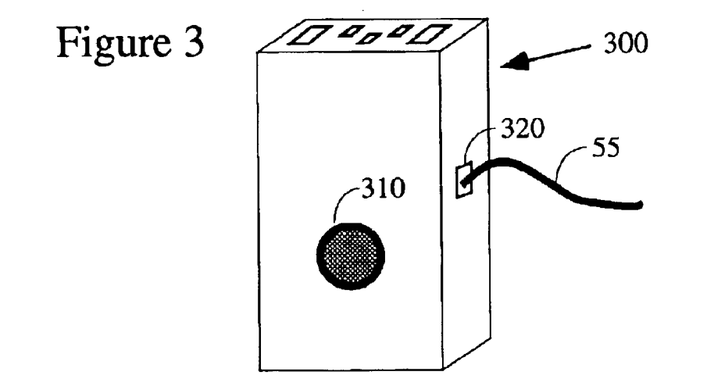
FIG. 3 contains an illustration of the external features of a preferred monitor embodiment.

Turning first to FIG. 3, a preferred embodiment of the instant invention 300 includes external speaker 310 which is preferably used both to broadcast white noise masking sounds and to sound an audible alarm upon the detection of a change in the monitored patient's condition. Preferably the speaker 310 will be a conventional cone-type speaker, although many other variations are certainly possible (e.g., a piezoelectric device, etc.). Of course, multiple speakers could be used (e.g., one to broadcast the white noise and another for the in-room alarm), but simple economics would generally suggest that generally a single speaker would be preferred. Of course, a mix of speaker types could be used depending on the particular application. Thus, in the text that follows the term "speaker" should be broadly construed to include a single speaker or multiple speakers (either located within the electronic monitor or positioned remotely and in electronic communication therewith) as the situation warrants.

According to the instant embodiment, the patient's at-rest position/orientation is preferably detected via a sensor 100 or 200 which might be a conventional pressure sensitive mat, a sensor that provides at least an approximate "X" and "Y" location of the patient (which might include such devices as a video camera, a grid of pressure sensitive sensors, a grid of temperature sensitive sensors, a grid of pressure sensors, etc.), or any number of other sensor combinations that allow the patient's approximate position and/or orientation on the support surface to be determined. For purposes of the instant embodiment, though, it is important that the sensor 100/200 at least be able to provide some ability to determine an approximate position and/or orientation of the patient in the bed so that a determination can be made as to when the patient has actually moved.

A connector 320 is preferably provided on the exterior of the monitor to accept a matching plug which is in electronic communication (e.g., via electrical line 55) with a sensor 100/200. Preferable, the sensor 100/200 will be disposable, the object of such an arrangement being to allow the sensors 100/200 to be interchanged without changing the more expensive attached electronic monitor 300. That being said, those of ordinary skill in the art will recognize that the sensor need not be disposable and, indeed, long term use sensors are offered by many in this industry. Additionally, interconnection by an electrical line 55 is only a preferred embodiment (e.g., consider wireless connectivity such as R.F., I.R., ultrasonic, etc., as those acronyms and terms are known to those of ordinary skill in the art).

Figure 4:
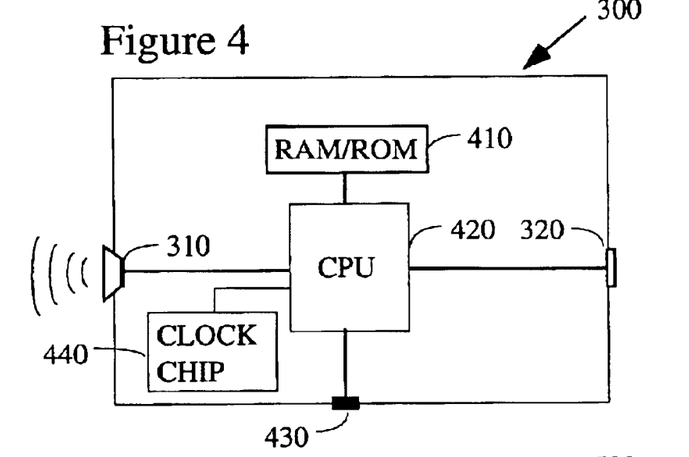
FIG. 4 is a schematic illustration of a preferred hardware configuration of the instant patient monitor.

Turning now to FIG. 4, wherein a preferred hardware schematic is illustrated, the instant monitor is preferably equipped with CPU/microprocessor 420 which is designed to execute computer instructions according to its internal programming. That being said, those of ordinary skill in the art will recognize that there are many active devices that could serve for purposes of the instant invention as the CPU 420 including, of course, a conventional microcontroller or microprocessor. More particularly, the term "microprocessor" as used herein minimally requires that the microprocessor 420 be an active device, i.e., one that is programmable in some sense, is capable of recognizing signals from a bed mat or similar patient sensing device, and is capable of digitally synthesizing alarm sounds (e.g., either via a mathematical algorithm or playback of a digital recording)—and/or instructing a separate sound generation module to generate such sounds—for broadcast by speaker 310. Of course, these sorts of modest requirements may be satisfied by any number of programmable logic devices ("PLD") including, without limitation, gate arrays, FPGA's (i.e., field programmable gate arrays), CPLD's, EPLD's, SPLD's, PAL's, FPLA's, FPLS, GAL, PLA, FPAA, PSoC, SoC, CSoC, ASIC, etc., as those acronyms and their associated devices are known and used in the art. Further, those of ordinary skill in the art will recognize that some of these sorts of devices contain microprocessors integral thereto. Thus, for purposes of the instant disclosure the terms "processor," "microprocessor" and "CPU" should be interpreted to take the broadest possible meaning herein, and such meaning is intended to include any PLD or other programmable device of the general sort described above.

Additionally, those of ordinary skill in the art will recognize that the instant invention could also be implemented using discrete logic and without using any sort of microprocessor. Note that, for purposes of the instant invention, and as has been described previously, a central function of the above-described microprocessor is to monitor the patient's position and activate/deactivate the white noise generator depending on the patient's movement (or lack of same). Those of ordinary skill in the art will recognize that it is readily possible to construct a discrete logic circuit that monitors the patient's position and activates a separate white noise generation circuit (which, itself, might or might not contain a microprocessor or other programmable device) depending on when the patient has last moved.

As is illustrated in FIG. 4, the microprocessor 420 will be placed into electronic communication with connector 320, through which it can determine the current status of the attached patient sensor 100/200. Additionally, it is preferred that a clock chip 440 or similar timing circuit be included within the monitor 300 for use thereby the microprocessor

420. That being said, it is well known to those of ordinary skill in the art that timing loops and other software implementations can be used in place of the clock chip 440 and such use has been specifically contemplated by the instant inventors. Additionally, it should be noted that it is certainly possible that the clock chip 440 might be incorporated into/made a part of the circuitry of the microprocessor 420, rather than being provided as a separate external circuit as is illustrated in the preferred embodiment of FIG. 4.

Speaker 310 is preferably located on the external surface of monitor 300 so that sounds, including alarm sounds and white noise sounds, can be broadcast into the patient's room. In the preferred arrangement, and as is illustrated in FIG. 4, a single speaker will be used both to sound alarms and to broadcast white noise according to the method described later. However, it should be clear that multiple speakers 310 might be used, e.g., one might be dedicated to the sounding of white noise and another for sounding alarm sirens. Indeed, it is not essential that either speaker be incorporated into the housing of monitor 300, but instead each might be housed apart from the monitor 300, e.g., the alarm speaker might be located in a hall or at the nurse's station, whereas the white noise speaker could be mounted in the wall of the patient's room, placed under the patient's pillow, etc. Those of ordinary skill in the art will be able to devise many such arrangements.

Preferably, the microprocessor 420 will be have access to some amount of RAM/ROM 410 which would be used to contain, among other things, the software that control's the monitor's 300 operations. Although FIG. 4 indicates that in the preferred arrangement the RAM/ROM 410 is separate from the microprocessor 420, those of ordinary skill in the art will recognize that in many cases microprocessors are available which have some small amount of RAM and/or ROM available internally. Thus, FIG. 4 should be understood to include those configurations where the computer memory is either internal or external to the microprocessor.

Figure 5:
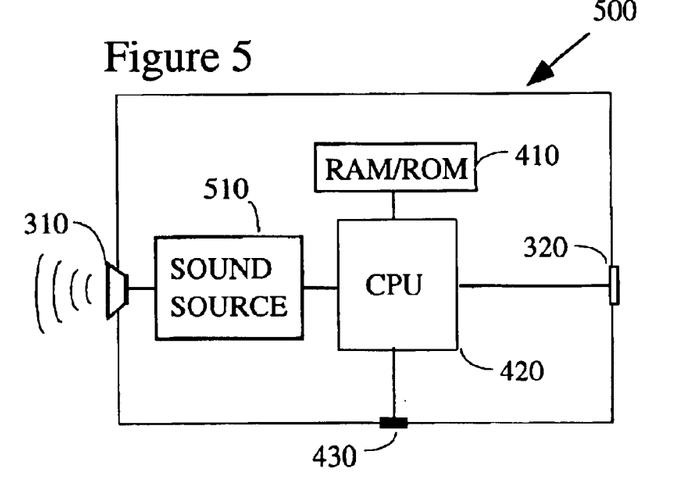
FIG. 5 contains another preferred embodiment of the instant patient monitor.

According to another preferred embodiment, and as is set out in FIG. 5, there is provided a patient monitor substantially as described above, but wherein the CPU 420 is in electronic communication with a separate sound source chip 510, which chip 510 generates all or part of the sound that is heard through speaker 310. That is, in one preferred arrangement the synthesizing chip 510 will begin to generate sound at the direction of the CPU 420 and will terminate its sounds upon the command of the CPU 420, after a predetermined time period, or according to some other scheme. As is described hereinafter, the sound source chip 510 generates masking sounds according to well known methods which might include synthesis of masking noise based on the mathematical generation of a white noise time series, playing a digital representation of a previously recorded white noise source (e.g., a recording of ocean waves, a waterfall, etc.), or any other similar arrangement. Additionally, the white noise generator might be something as simple as an FM receiver or similar circuit which has been tuned to an interval in the broadcast spectrum where there are no stations (i.e., "static" will be received). In the instance that prerecorded sounds are chosen as the marking noise source, the instant inventors have contemplated that the sound source 510 might be a chip as simple as an ISC 1500-type chip (a so-called "bucket brigade" chip) which allows simple recording and playback of audio information. Alternatively, a single-chip synthesizer or a multi-chip sound generator are also possible. Those of ordinary skill in the art will recognize that many alternatives are possible.

Figure 6:
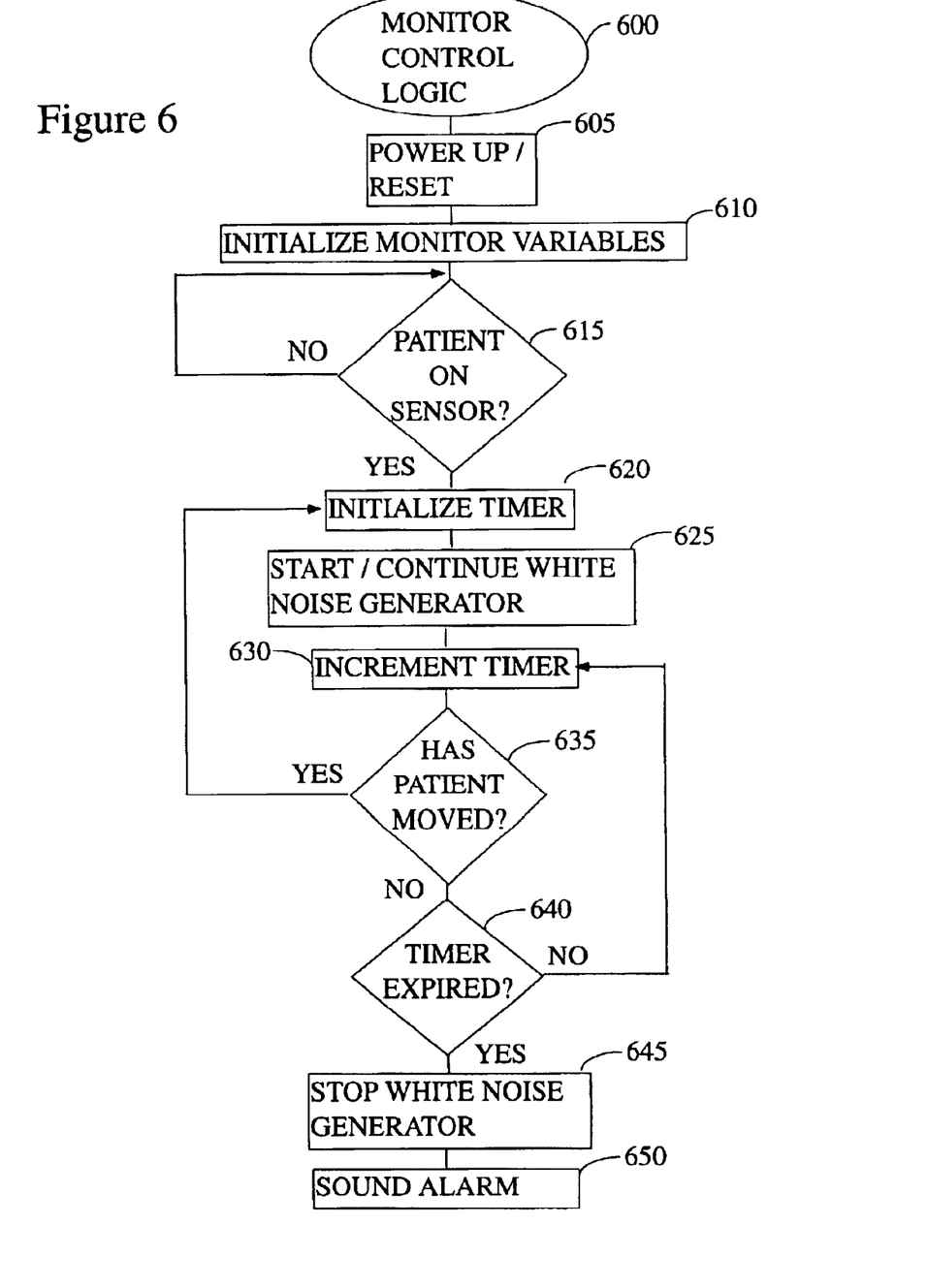
FIG. 6 contains a schematic illustration of a preferred control logic for use by the microprocessor of the instant patient monitor when configured as a decubitus ulcer monitor.

According to another preferred embodiment, there is provide in FIG. 6 a monitor control logic 600 suitable for use with the instant invention. As is generally indicated in this figure, at reset or power-up 605 a number of system-level functions might be performed (e.g., checking for sensor integrity, verifying connectivity with the nurses station, etc.), among which would preferably include initializing various monitor variables 610 and timers, etc.

As a next preferred step, the monitor will enter a loop which continuously checks 615 to see whether or not a patient is proximate to the attached sensor. In the event that the attached sensor is a bed mat 100 or similar pressure sensitive sensor, the program preferably loops until the patient's presence is sensed on the mat 100.

After a patient has been detected on the sensor 100 (or in the event that the caregiver manually activates the unit) a timer will be initialized 620. Preferably, and as is described more fully hereinafter, this timer will be used to measure the length of time that the patient remains motionless. Alternatively, instead of "zeroing" a counter the current time of day might be noted and saved for later comparison at step 640.

As a next preferred step, the white noise generator will be activated 625. As has been described previously, in a preferred arrangement the white noise sound source will be broadcast to the patient via speaker 310 which is preferably positionable to be within earshot of the patient. Next, the timer variable will preferably be incremented 630 as part of the patient monitoring loop 630, 635, and 640. Additionally, one or more "wait" states might be introduced into the loop in a manner well known to those of ordinary skill in the art.

As a next preferred step, the program will determine whether or not the patient has changed position 635 since the time of the previous check. If the patient has so moved, the monitor will preferably reset the timer 620 and continue sounding white noise. If the patient has not moved, the program will next preferably check to see whether a sufficient period of time has elapsed 640 that the patient should be encouraged to move. In one preferred arrangement, the elapsed time since the patient last moved will be compared 640 with a predetermined turn interval for this patient. If it is not time for the patient to turn, the program preferably returns to step 630 and continues to monitor for patient movement activity.

On the other hand, if the comparison 640 indicates that it is time for the patient to move, the monitor preferably will cease 645 the sounding of white noise. The cessation of the heretofore constant sound source will make it more likely that the patient will be roused from slumber if activity is taking place around him or her and, thus, increase the probability that the patient will rouse him or herself and change position. Alternatively, rather than suddenly ceasing the broadcast of the masking noise, the monitor could instead slowly lower the volume to the point where it becomes inaudible, the hope being that during the time the volume is being reduced the patient will be lead to move on his/her own before intervention is required. Of course, upon the monitor making a determination that the patient has moved, the volume of the masking sound will be returned to its original volume (either immediately or via a ramped increase), thereby making it more comfortable for the patient to rest again.

Optionally, after the broadcast of the masking sound volume has been stopped the instant method will leave the patient in silence for some period of time, e.g., ten minutes, during which time the patient's position will continue to be monitored. The purpose of this step is to see whether removal of the masking sounds can induce the patient to move on his/her own. If so, and as described previously, the masking sounds will be reinstated. However, in another preferred arrangement, if the patient has not moved by the end of the period of silence, the monitor will preferably begin to generate a soft beep or other sound that is calculated to gain the patient's attention. Preferably this will be a precursor to the sounding of the alarm 650. The purpose of this step is to further encourage patients to roll over or otherwise change position on their own. In the event that the patient has been sleeping, the beep or other sound will tend to rouse him or her. Preferably, this sound will be slowly increased in volume until either a maximum predetermine volume has been reached, or until the patient moves, or until some predetermined time period is exceeded, e.g., ten minutes. That is, the patient will preferably be given some additional period of time after the termination of the masking sound to see whether it is possible to convince the patient to move before summoning a caregiver, as is discussed below.

Of course, if the patient does not change position on his or her own initiative, it is preferred that this information be communicated to the caregiver 650 so that the patient may be turned manually. In a preferred arrangement, a bed-side alarm will be initiated (e.g., via speaker 310) which will, of course, tend to wake the patient so that when the caregiver arrives the patient will potentially be ready to be moved.

Figure 7:
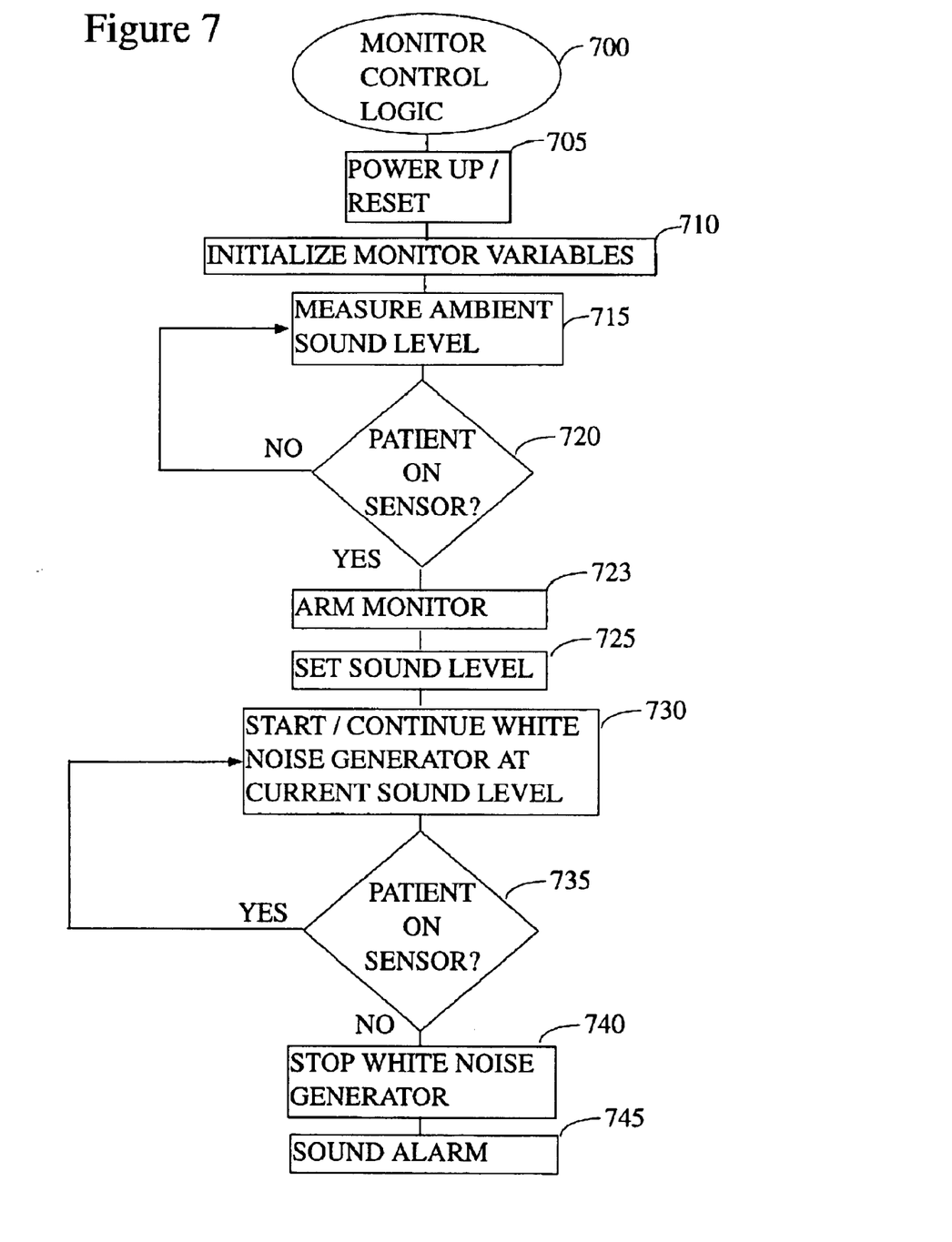
FIG. 7 illustrates a preferred logic for use when the white-noise generating patient monitor is configured to be a patient exit monitor.

According to another preferred arrangement and as is generally illustrated in FIG. 7, there is provided a system and method substantially as described above, but wherein the white noise volume is adaptively determined by the microprocessor. As is set out in program logic 700, preferably upon initial power-up/reset 705 of the monitor, various program variables will be initialized 710. Additionally, it is preferred that the monitor determine the level of ambient sound in the vicinity of the patient 715. Although this might be done in many ways, preferably this determination will be made either by inclusion within the embodiments of FIG. 4 or 5 a separate microphone accessible by microprocessor 420. Alternatively, and as is well known to those of ordinary skill in the art, the microprocessor 410 can obtain at least a crude estimate of the ambient sound level by "reading" speaker 310. The practicality of doing this should become more apparent when it is recognized that there is no need to obtain an accurate recording of the ambient sound, but only an estimate of its current level.

As a next step, and has been described previously, a loop 715/720 will preferably be executed until such time as the patient is sensed to be present. Alternatively, of course, the microprocessor could be put to "sleep" and then automatically "waked" (e.g., via an interrupt line) when a patient is present. In this later case, an event loop would not be necessary but, instead, the microprocessor could simply "wait" for a patient to arrive. In either case, once the patient has been detected the monitor will preferably automatically arm 723 and set the sound level of white noise 725 according to the ambient noise level measured previously (step 715). That is, in the preferred arrangement the output sound level of the microprocessor will be varied according to the measured ambient sound level, with the white noise being made louder if the measure of the ambient sound level 715 indicates that the environment is "noisy". Similarly, if the measured ambient noise level is lower, the volume of the white noise sounds will be correspondingly decreased.

Next, the software preferably enters a "monitor" phase, during which time it continuously checks for the patient's presence (steps 735 and 730). If the patient is still present (the "YES" branch of step 735), the preferred logic has the microprocessor continue the generation of white noise at the current level (step 730) and then subsequently check for the patient's presence again (step 735).

However, if the microprocessor determines that the patient is not on the sensor (the "NO" branch of step 735), the microprocessor preferably terminates generation of the white noise (step 740) and sounds an audible alarm 745, either through the patient monitor's 300 own internal speaker 310, remotely at the nurses station, or elsewhere.

Of course, it should be clear that optionally the software logic of the patient monitor might provide for continuously modifying the current white noise sound level (e.g., as a component of step 730) as a function of the then-current noise level near the patient. That is, in another preferred arrangement, the ambient sound level will be periodically redetermined and the white noise volume level adjusted up or down accordingly.

According to a further preferred embodiment of the instant invention, there is provided an electronic patient monitor substantially as described above, but wherein the center frequency of the white noise is tunable to mask ambient noise of a specific frequency content. That is, it may well be that the ambient noise near a patient is not broadband, but instead is concentrated in a few frequencies, or within a relatively narrow range of frequencies. The monitor, given the frequency of the ambient noise, could then adaptively "color" the frequency spectrum of the white noise to match the then-present noise conditions.

Figure 8:
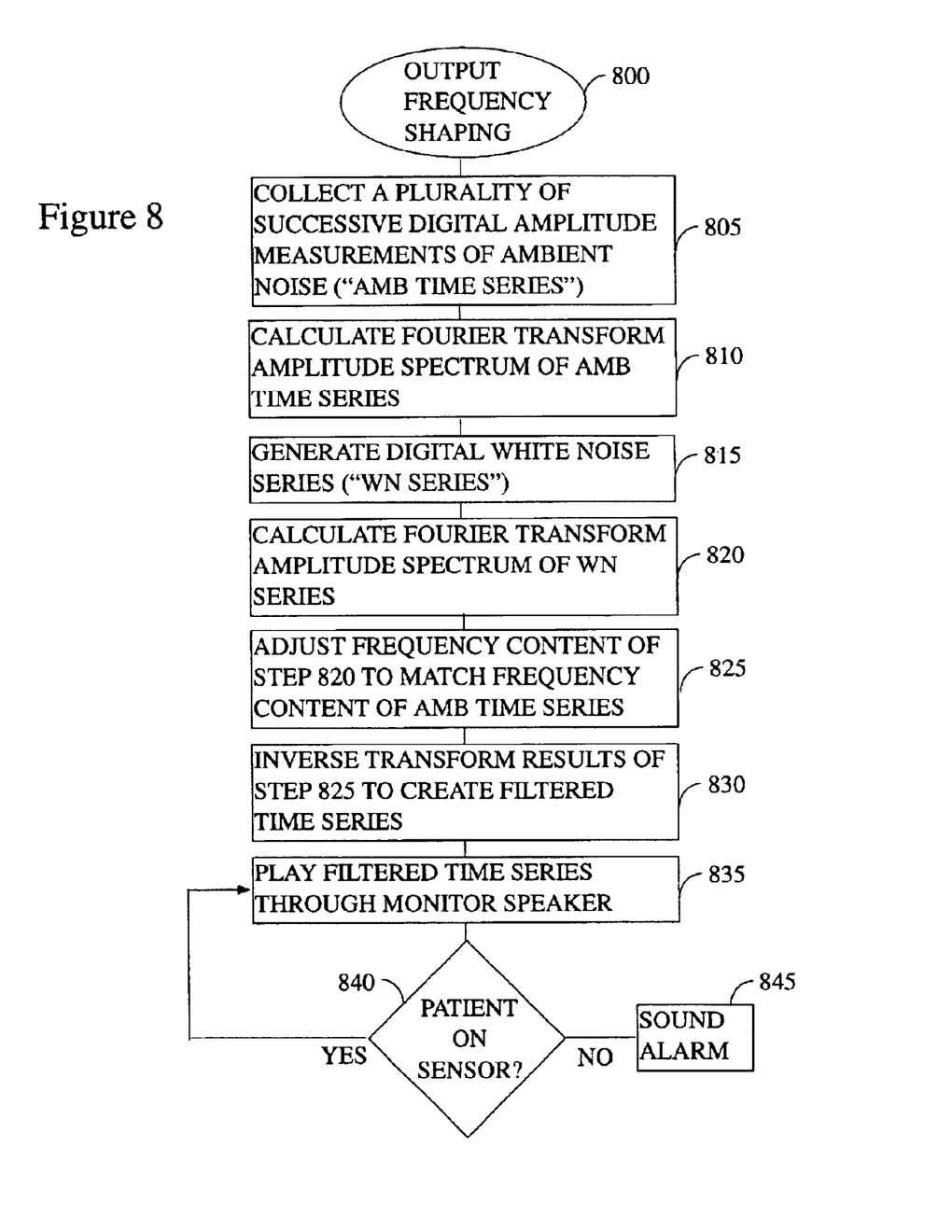
FIG. 8 contains a schematic illustration of a preferred control logic of the instant invention wherein frequency shaping of the white noise output is utilized.

This operation could readily be incorporated into steps 715 and 730 of FIG. 7 as follows. As is illustrated in FIG. 8, a preferred arrangement of the instant embodiment begins with the collection of a finite length time series (at some known sample rate) which is composed of ambient noise volume measurements (step 805). Preferably, the sample rate (i.e., rate at which the ambient noise is sampled by the monitor) should at about twice the highest frequency that is to be synthesized, 22 kHz or 44 kHz would likely be adequate for most applications, although the actual sample rate could certainly be adjusted up to down depending on the exact sonic characteristics of the noise at a particular facility. Preferably, the length of time over which the ambient noise will be sampled would be at least 30 times the lowest period of the lowest noise frequency to be synthesized. Five seconds of ambient noise data are collected in one preferred arrangement. As a next preferred step, the frequency content of the sampled ambient noise will be determined, preferably by calculating the Fourier transform amplitude spectrum of the ambient noise time series (step 810). As is well known to those of ordinary skill in the art, the spectral values so-obtained will provide estimates of the frequency content of the ambient noise. Note that steps 805 and 810 could readily be made a part of step 715 in FIG. 7.

Then, and according to a preferred arrangement, during the white-noise generation step 730, the output white noise will be filtered to cause its frequency spectrum to match the frequency content of the ambient noise. One way of doing that would be to, first, generate a scaled white-noise time series of some predetermined number of samples in length 815. The Fourier transform amplitude spectrum of the white noise time series would next be calculated 820. Of course, if the white noise generation algorithm is operating perfectly, the calculated amplitude spectrum would be expected to be "flat", i.e., to contain all frequencies in equal proportion. However, more generally, it is likely that the calculated spectrum will have some sort of "shape." As a next preferred step, the white noise time series will be filtered in the frequency domain so that its spectrum at least approximately matches that of the ambient noise (step 825). Those of ordinary skill in the art will recognize that this could be done in any number of ways.

As a next preferred step, the filtered frequency spectrum will be inverse transformed (i.e., transformed back into the time domain) 830 and "played" through the speaker (step 830) at a predetermined sample rate according to methods well known to those of ordinary skill in the art. The sound that is emitted from the speaker will now be at least roughly be matched to the frequency content of the ambient noise. Of course, imperfections in the frequency response characteristics of the monitor speaker 310 will further shape the actual sound output and these imperfections can be at least approximately compensated for according to standard methods.

As is generally indicated in FIG. 8, it is anticipated that the same filtered time series can be repeatedly and continuously played 835 (e.g., by looping the series). In a preferred arrangement, if the status of the patient changes (e.g., by the patient leaving the mat, the "no" branch of step 840) the monitor will preferably terminate the generation of white noise and sound the alarm 845.

According to still a further preferred embodiment, there is provided a electronic patient monitor substantially as described above, but wherein the monitor has at least two different operating "modes": a first mode wherein the patient's unassisted/independent movement is evaluated ("evaluation" mode), and a second mode wherein the patient is continuously monitored and the white noise generator is activated or not depending on the patient's current activities as measured against the level of activity observed during the evaluation phase. Note that it is preferred that none of the sound-masking features be activated during the "evaluation mode", so that an accurate baseline of the patient's self-movement pattern can be established. The well known "Braden Scale" or similar scale for assessing the risk of decubitus ulcers in patients might be used to select candidate patients for evaluation.

Preferably, during the time that the electronic monitor is in its evaluation mode, the patient will be continuously monitored to establish a baseline movement pattern. In the preferred arrangement, the patient will be monitored for several hours, perhaps over night or over a 24 hour period. Of course, during the evaluation period the masking sounds described previously will not be utilized so that an accurate measurement of the patient's movement level may be established.

In a preferred arrangement, the sensor 100 that will be used to detect patient movement will be one that can be used to determine at least approximately the "X" and "Y" coordinates of the patient's location on the sensor 100. More preferably, the sensor 100 will provide the "X" and "Y" coordinates of the contact points of the patient with the sensor 100. One sensor that would be suitable for this purpose would be a sensor that has a grid of separately readable contact points so that the patient's exact position on the sensor—together with his or her contact area—can be determined. Of course, given the contact area(s) of the patient with the sensor 100 as those areas change over time, it will be possible to accurately track the amount of movement and the duration of each move that the patient makes.

According to a further embodiment, there is provided a electronic patient monitor 300 substantially as described above, but wherein the "white noise" source is drawn from a recording (either digital or analog) of the ambient sounds at the patient's home. In one preferred arrangement, the patient (or his/her family, if the patient is already hospitalized) will make a digital recording of ambient house sounds at the patient's residence (e.g., refrigerator, dish washer, washing machine, dryer, animals in or around the house, air conditioner/heater, etc.). The recording, or some edited or summarized portion thereof, will then be transferred to the instant electronic monitor where it is preferably held in digital form within the memory of the monitor until such time as it would be appropriate to play "white noise" for the patient.

During such playback, one of two possible modes will preferably be employed. In a first mode, the patient's own recorded home sounds will be played at a level that masks facility noise, thereby replacing the unfamiliar ambient sounds with more familiar ones. In a second preferred mode, conventional white noise will be played together with the patient's own ambient home sounds, thereby more completely masking intrusive noises at the facility. That is, in this mode the electronic monitor will preferably digitally combine the recording from the patient's home with a "true" randomly generated white noise "background" to create a composite sound source which is played as required. In this combination, the true white noise will tend to provide a base level sound source that will tend to mask most facility sounds. Then the other home-derived ambient sounds, which may contain "gaps" or "quiet" sections therein, will be played atop of the white noise series, make the patient more comfortable by providing sounds that are familiar to him or her, albeit in another setting. Additionally, and in some preferred arrangements, when the monitor determines that it is time for the patient to be moved it will cease the broadcast of, say, the underlying white noise while continuing to broadcast the home sounds, the hope being that by doing this the patient will be roused somewhat and move on his or her own. After some period of time, say ten minutes, the second masking sound source (e.g., the home sounds) will be terminated, thereby resulting in the cessation of all masking sound broadcasts. As has been described previously, it is preferred that a period of silence follows the cessation of the masking noise broadcast (e.g., ten minutes) to allow the patient an opportunity to turn him or her self, after which the caregiver would typically be notified that it was time to turn this patient.

According to still another preferred embodiment, there is provided an electronic patient monitor substantially as described above, but wherein the monitor is configured to provide active noise cancellation in concert with—or as an alterative to—white noise generation to reduce the level of ambient noise proximate to the patient. That is, there is provided hereinafter a patient monitor substantially as described above but wherein the monitor contains an active noise reduction system to reduce the level ambient noise experienced by the patient.

As is well known to those of ordinary skill in the art, "active noise reduction" or "active noise control/cancellation" is a field of technology that seeks to reduce the perceived noise level by creating "anti-noise" which is interferes destructively with the incoming noise field, thereby reducing its amplitude. There are two basic approaches to noise cancellation, one of which involves structural-acoustic control and the other which implicates active noise cancellation. The instant embodiment is concerned with the latter type of noise cancellation.

Figure 9:
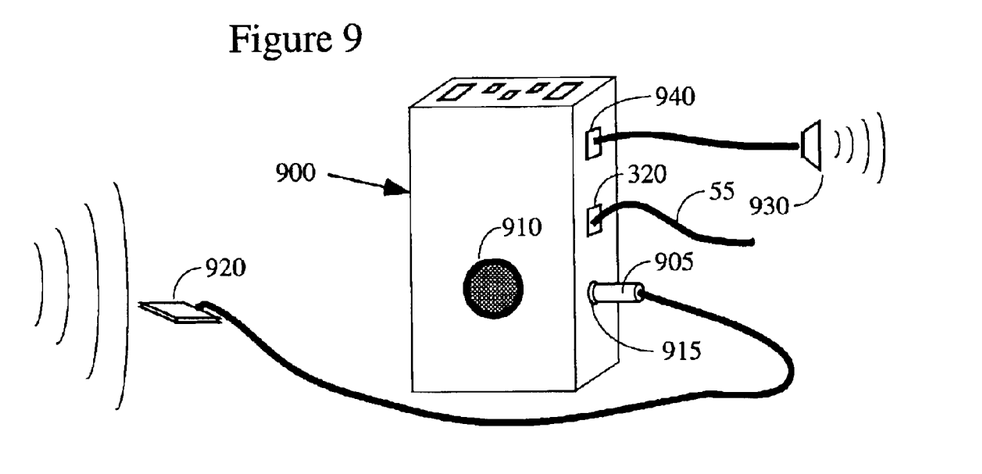
FIG. 9 illustrates a preferred embodiment wherein a separate microphone is used in connection with noise cancellation.

Although active noise cancellation might be implemented in many ways, in a first preferred arrangement and as is generally illustrated in FIG. 9, a separate microphone located between the patient and the door will pick up ambient noise from the facility as it enters the room on its way to the patient. The monitor 940 will then generate and broadcast sound that is approximately 180 degrees out of phase with that coming in through the door, thereby reducing the level of ambient noise experienced by the patient.

Figure 10:
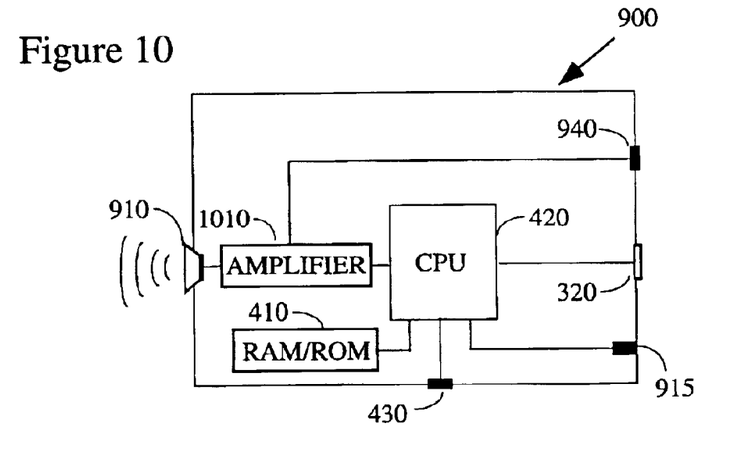
FIG. 10 contains a schematic illustration of the preferred patient monitor of FIG. 9.

Turning now to FIGS. 9 and 10, in a preferred arrangement the patient monitor 900 will be generally configured as has been described previously, with a CPU 420, memory 410, a connector 320 for communicating with a patient sensor 100, etc. Additionally, the instant invention is preferably equipped with at least one microphone 920 for sensing and transmitting to the CPU 420 ambient noise. Note that the microphone 920 might be positioned apart from the microprocessor 420 and connected thereto by connector 905 and jack 915 as is illustrated in FIGS. 9 and 10, or it might be located internal to the monitor 900. In the event that an internal microphone is desired, it will preferably be a conventional microphone or other device suitable for sensing ambient sound levels. Additionally, those of ordinary skill in the art will recognize that multiple microphones might be employed to increase the effectiveness of the noise suppression.

Additionally, and depending on the particular application, in some cases a separate external speaker 930 may be utilized which is driven through external audio connector 940. Preferably, such speaker will be positioned proximate to the patient, so as to be situated to cancel the in-coming noise as much as is possible. In such an instance, there also may be a need for a more powerful amplifier 1010 (FIG. 10) than would ordinarily be used to drive the small internal speaker 910. Obviously, separate amplifiers could also be used to drive the speakers 910 and 930. Additionally, although it is contemplated that the microprocessor 420 will synthesize the noise-canceling sounds, it should be clear that a separate digital signal processing ("DSP") chip or other arrangement might be interposed between CPU 420 and amplifier 1010, which DSP chip would operate under the direction of the microprocessor 420 to implement active noise cancellation based on signals received from microphone 920.

Although there are many different ways in which active noise cancellation could be implemented, one preferred arrangement involves the use of an analog or digital "inverter", as that term is known and understood in the art. That is, preferably the signal of ambient noise arriving from microphone 920 will be delayed (depending on the microphone 920–monitor 900 distance) and inverted before being rebroadcast. The inversion process in effect creates an output signal that is 180 degrees out of phase with the incoming noise signal and, provided that the signal is delayed appropriately, will tend to cancel the incoming noise. The amount of delay might be determined in many ways, but clearly given the distance between the microphone 920 and the monitor 900 and/or speaker 930, this delay may be readily calculated from the known speed of sound in air. Obviously, to the extent that the amount of delay is accurately calculated, the output from the speakers 910 and/or 940 will do a better job of canceling the ambient noise, with high frequency noise being more sensitive to the correct determination of the amount of delay than low frequency noise.

The embodiment described previously is a so-called "feed forward" system of control, in that the microphone is locate upstream at a distance from the monitor 900 sufficient to enable some calculations to be performed prior to generating the output/canceling signal. If only a single microphone located at the monitor 900 is used, the methodology used would be more in the nature of a "feedback" system tends to be less stable in its implementation and less effective at high frequencies.

CONCLUSION

It should be noted and remembered that the preferred electronic monitor includes programming instructions stored therein for execution by the microprocessor, which programming instructions define the monitor's response to the patient and environmental sensors. Although ROM is the preferred apparatus for storing such instructions, static or dynamic RAM, flash RAM, EPROM, PROM, EEPROM, or any similar volatile or nonvolatile computer memory could be used. Further, it is not absolutely essential that the software be permanently resident within the monitor, although that is certainly preferred. It is possible that the operating software could be stored, by way of example, on a floppy disk, a magnetic disk, a magnetic tape, a magneto-optical disk, an optical disk, a CD-ROM, a flash RAM device, a ROM card, a DVD disk, or loaded into the monitor over a network as needed. Additionally, those of ordinary skill in the art will recognize that the memory might be either internal to the microprocessor, or external to it, or some combination. Thus, "program memory" as that term is used herein should be interpreted in its broadest sense to include the variations listed above, as well as other variations that are well known to those of ordinary skill in the art.

Additionally, and as discussed previously, it should be clear to those of ordinary skill in the art that the masking sounds described above could easily be synthesized directly by the microprocessor, by a separate chip under control of the microprocessor, or by a "voice chip" or similar hardware sound recording device. Thus, in the text that follows, when the term "generate" is used in connection with the creation of masking or other sounds, that term should be interpreted in its broadest sense to include those situations where the microprocessor itself "generates" the masking sound, as well as those cases where the microprocessor directs a separate hardware component to produce the sound.

Further, note that the preferred masking sound of the instant invention could be chosen to be any regular/steady sound source that would tend to reduce the perceptibility of ambient noise in the patient environment. As has been discussed previously, conventional white noise sources (both from nature and mathematical) are ideal candidates, as are ambient sounds recorded from the patient's own house, etc. Additionally, since the preferred masking sounds are those that maintain a relatively steady level and/or exhibit a regular pattern of increase and decrease (e.g., ocean waves), certain types of music might also serve as a masking sound. It should be noted, however, that although it is known in the art to use music as an alarm sound (e.g., a song, rather than a strident alarm, is played when the patient leaves the bed), such a use is different from that taught herein where music is used as a masking sound before (or potentially during) the time when an alarm is sounded.

Note also that it is preferred that the monitor be provided with some sort of communications capability to that parameters, recorded sounds, programming instructions, etc., can be transferred to the monitor for use thereby. There are many communications links that would serve this purpose including wireless connectivity, transfer via direct download from a laptop or other computer, etc. Additionally, it is preferred that this same communications conduit be used to transfer back to a host computer information that has been accumulated by the monitor concerning the patient and/or his environment including without limitation, information such as a record of the patient's movement pattern over some time period as perceived by the monitor, a recording or analysis of the ambient noise detected by the monitor (e.g., to help determine the noise level of the facility as measured within the patient's room), etc. Those of ordinary skill in the art will recognize that there is a wealth of information about the patient and the facility environment that could be collected and analyzed by such a preferred patient monitor.

Finally, it should be noted that the term "nurse call" as that term has been used herein should be interpreted to mean, not only traditional wire-based nurse call units, but more also any system for notifying a remote caregiver of the state of a patient, whether that system is wire based or wireless. Additionally, it should be clear to those of ordinary skill in the art that it may or may not be a "nurse" that monitors a patient remotely and, as such, nurse should be broadly interpreted to include any sort of caregiver, including, for example, untrained family members and friends that might be signaled by such a system.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. An electronic patient monitor for use with a patient sensor, said patient sensor at least for detecting a presence or an absence of a patient, comprising:
    (a) a microprocessor in electronic communication with said patient sensor,
    (b) program memory in electronic communication with said microprocessor, said program memory containing a plurality of computer instructions therein for use by said microprocessor, said computer instructions containing at least at plurality of instructions for
    (b1) monitoring said patient sensor and initiating an alarm if the sensor indicates the absence of the patient, and,
    (b2) generating at least one masking sound if the sensor indicates the presence of the patient;
    (c) a speaker in electronic communication with said microprocessor, said speaker at least for broadcasting said at least one masking sound.

2. An electronic patient monitor according to claim 1, wherein said computer instruction for generating at least one masking sound, comprises at least a plurality of computer instructions for signaling to a sound source to generate said at least one masking sound.

3. An electronic patient monitor according to claim 1, further comprising:
    (d) an amplifier in electronic communication with said CPU and with said speaker, said amplifier for amplifying said at least one masking sound for broadcast through said speaker.

4. An electronic patient monitor according to claim 1, wherein said computer instructions for generating at least one masking sound, comprise a plurality of computer instructions for generating white noise sounds.

5. An electronic patient monitor according to claim 1, wherein is provided a sound recording of ambient sounds from the patient's home, and wherein said computer instructions for generating at least one masking sound, comprise a plurality of computer instructions for initiating a playback through said speaker of said sound recording of ambient sounds.

6. An electronic patient monitor according to claim 1, wherein said speaker is both for broadcasting said at least one masking sound and broadcasting said initiated alarm.

7. An system for reducing the risk of an occurrence of decubitus ulcers in a patient at rest on a support surface, wherein is provided a predetermined turn interval, comprising:
    (a) a patient sensor, said patient sensor positionable to be proximate to the patient, said patient sensor at least for sensing at least approximately an orientation of the patient on the support surface and for generating at least one signal representative of said orientation of the patient on the support surface; and,
    (b) a patient monitor positionable to be in electronic communication with said patient sensor, said patient monitor comprising:
        (b1) a microprocessor in electronic communication with said patient sensor,
        (b2) a speaker in electronic communication with said microprocessor, said speaker positionable to be proximate to the patient;
        (b3) program memory in electronic communication with said microprocessor, said program memory containing a plurality of computer instructions therein for use by said microprocessor, said computer instructions containing at least a plurality of instructions for
            (i) monitoring said signal representative of said orientation of the patient on the support surface to determine an initial position of the patient,
            (ii) generating a masking sound while monitoring said signal representative of said orientation of the patient,
            (iii) transmitting said masking sound to said speaker,
            (iv) broadcasting said masking sound within hearing range of the patient;
            (v) determining a time since said initial patient position was determined,
            (vi) performing steps (ii) through (v) at least until either said time since said initial patient position was determined exceeds said predetermined turn interval, or until the patient changes position from said initial position which ever occurs first, and,
                if said time since said initial patient position was determined exceeds said predetermined turn interval, ceasing generation of said masking sound and generating an alarm after a predetermined time delay, and,
                if the patient changes position from said initial position, redetermining said initial position and continuing to monitor the patient.

8. An electronic patient monitor according to claim 7, wherein said computer instructions for generating a masking sound, comprise at least a plurality of computer instructions for signaling to a sound source to generate said masking sound.

9. A method for reducing the risk of an occurrence of decubitus ulcers in a patient at rest on a support surface, comprising the steps of:
    (a) selecting a turn interval;
    (b) determining an initial position of the patient;
    (c) generating a masking sound;

(d) broadcasting said masking sound within a hearing range of the patient, thereby enhancing the patient's rest by making inaudible at least a portion of the ambient sounds otherwise audible by the patient;

(e) continuing to broadcast said masking sound within the hearing range of the patient while continuously monitoring the patient's current position;

(f) determining a time since said initial position was determined;

(g) performing steps (c) through (f) at least until said time since said initial patient position was determined exceeds said predetermined turn interval; and, (h) if said current position of the patient is not substantially different from said initial condition, sounding an alarm to notify a caregiver that the patient needs to be turned and controlling the generation of said masking sound by either ceasing or continuing broadcast of said masking sound.

10. A method for reducing the risk of an occurrence of decubitus ulcers in a patient according to claim 9, wherein step (e) comprises (h1) terminating the broadcast of said masking sound, and, (h2) sounding an alarm to notify a caregiver that the patient needs to be turned.

11. A method for reducing the risk of an occurrence of decubitus ulcers in a patient according to claim 9, wherein is provided a predetermined time period, said predetermined time period being less than said turn interval, and wherein step (e) comprises:

(e1) continuing to broadcast said masking sound within the hearing range of the patient while continuously monitoring the patient's current position if said time since said initial position was determined is less than said predetermined time period, thereby encouraging the patient to continue resting, and, (e2) ceasing to broadcast said masking sound and continuing to continuously monitoring the patient's current position if said time since said initial position was determined is greater than said predetermined time period and less than said turn interval, thereby encouraging the patient to change position.

12. A method of reducing the risk of an occurrence of decubitus ulcers in a patient, wherein is provided a patient sensor positionable to be proximate to the patient, said patient sensor at least for determining an approximate position of the patient, and wherein is provided a predetermined turn interval, comprising the steps of:

(a) determining an initial position of the patient from said patient sensor;

(b) beginning to broadcast a masking sound within hearing range of the patient;

(c) continuing to broadcast said masking sound while monitoring the patient's position;

(d) determining a current position of the patient using said patient sensor and determining an elapsed time since said initial position of the patient was determined;

(e) comparing said initial position of the patient with said current position of the patient to determine if the patient has moved, and, (i) if the patient has moved from said initial position, continuing to broadcast said masking sound while continuing to monitor the patient's position, (ii) if the patient has not moved from said initial position and said elapsed time is less than said predetermined turn interval, continuing to broadcast said masking sound while continuing to monitor the patient's position, and, (iii) if the patient has not moved from said initial position and said elapsed time is greater than said predetermined turn interval, sounding an alarm to indicate the patient needs to be turned and controlling the generation of said masking sound by either ceasing or continuing broadcast of said masking sound.

13. A method according to claim 12, wherein step (iii) comprises the step of:

if the patient has not moved from said initial position and said elapsed time is greater than said predetermined turn interval, ceasing to broadcast said masking noise and sounding an alarm to signal that the patient needs to be turned.

14. A method of reducing the risk of an occurrence of decubitus ulcers in a patient according to claim 12, wherein is provided a predetermined time period which is less than said predetermined turn interval, and wherein step (e)(ii) comprises the step of:

(1) if the patient has not moved from said initial position and said elapsed time is less than said predetermined turn interval and said elapsed time is less than said predetermined time period, continuing to broadcast said masking sound while continuing to monitor the patient's position, and, (2) if the patient has not moved from said initial position and said elapsed time is less than said predetermined turn interval and said elapsed time is greater than said predetermined time period, ceasing broadcast of said masking sound while continuing to monitor the patient's position, thereby encouraging the patient to move.

15. An electronic patient monitor for use with a patient sensor, said patient sensor at least for detecting a presence or an absence of a patient, comprising:

(a) at least one microphone positionable to be proximate to said patient, said microphone for sensing ambient sounds proximate thereto, (b) a microprocessor in electronic communication with said patient sensor and with said at least one microphone;

(c) a speaker in electronic communication with said microprocessors, (d) program memory in electronic communication with said microprocessor, said program memory containing a plurality of computer instructions therein for use by said microprocessor, said computer instructions containing at least a plurality of real-time instructions for (b1) monitoring said patient sensor and initiating an alarm if the sensor indicates the absence of the patient, (b2) obtaining from said at least one microphone at least one input signal representative of said ambient sounds proximate to the patient, (b3) using at least a portion of said at least one input signal to generate an output signal that at least in part interferes destructively with said input signal, and, (b4) broadcasting said output signal via a speaker, thereby reducing the volume of the ambient noise proximate to the patient, and (b5) controlling said broadcasting of said output signal based on the patient's detected presence or absence.

16. An electronic patient monitor for use with a patient sensor, said patient sensor at least for detecting a presence or an absence of a patient, comprising:

(a) a patient detection circuit in electronic communication with said patient sensor, said patient detection circuit at least for
  (a1) detecting a presence or an absence of a patient from the sensor,
  (a2) initiating an alarm if the patient's absence from the sensor is detected, and,
  (a3) initiating the generation of a masking sound in response to the detection of the patient's presence on the sensor;
(b) a masking sound generation circuit, said masking sound generation circuit being responsive to said patient detection circuit to produce at least one masking sound based on the patient's detected presence or absence;
(c) a speaker in electronic communication with said masking sound generation circuit, said speaker at least for broadcasting said at least one masking sound.

17. An electronic patient monitor according to claim 16, wherein said patient detection circuit comprises:

(a1) a microprocessor in electronic communication with said patient sensor, said microprocessor containing a plurality of computer instructions therein, said computer instructions comprising at least a plurality of instructions for:
  (i) monitoring said patient sensor and initiating an alarm if the patient sensor indicates the absence of the patient, and,
  (ii) signaling to said masking sound generation circuit to begin the generation of said masking noise after detection of the patient's presence upon the patient sensor.

* * * * *